(12) United States Patent
Bax et al.

(10) Patent No.: US 9,726,517 B2
(45) Date of Patent: Aug. 8, 2017

(54) MECHANICAL TRACKING SYSTEM

(71) Applicants: University of Western Ontario, London (CA); Centre for Imaging Technology Commercialization, London (CA)

(72) Inventors: Jeffrey Bax, London (CA); Aaron Fenster, London (CA)

(73) Assignee: Centre for Imaging Technology Commercialization (CA)

( * ) Notice: Subject to any disclaimer, the term of this patent is extended or adjusted under 35 U.S.C. 154(b) by 94 days.

(21) Appl. No.: 14/414,541

(22) PCT Filed: Jul. 15, 2013

(86) PCT No.: PCT/CA2013/000631
§ 371 (c)(1),
(2) Date: Jan. 13, 2015

(87) PCT Pub. No.: WO2014/012163
PCT Pub. Date: Jan. 23, 2014

(65) Prior Publication Data
US 2015/0168179 A1   Jun. 18, 2015

Related U.S. Application Data

(60) Provisional application No. 61/671,701, filed on Jul. 14, 2012.

(51) Int. Cl.
*G01B 7/30*      (2006.01)
*G01R 33/02*     (2006.01)
(Continued)

(52) U.S. Cl.
CPC .............. *G01D 5/14* (2013.01); *A61B 5/055* (2013.01); *A61B 6/032* (2013.01); *A61B 8/085* (2013.01);
(Continued)

(58) Field of Classification Search
CPC . G01D 5/14; G01D 5/26; A61B 90/11; A61B 34/20; A61B 8/483; A61B 8/4218;
(Continued)

(56) References Cited

U.S. PATENT DOCUMENTS

| | | | |
|---|---|---|---|
| 5,898,599 A | 4/1999 | Massie et al. | |
| 2011/0206481 A1* | 8/2011 | Al-Mouhamed | B25J 9/104 414/5 |
| 2012/0153946 A1* | 6/2012 | van Veldhoven | G01D 5/2451 324/252 |

FOREIGN PATENT DOCUMENTS

| | | |
|---|---|---|
| WO | 2009039659 A1 | 4/2009 |
| WO | 2013142978 A1 | 10/2013 |

OTHER PUBLICATIONS

Supplementary European Search Report corresponding to EP13820683, dated Jan. 27, 2016, 9 pages.

\* cited by examiner

*Primary Examiner* — Farhana Hoque
(74) *Attorney, Agent, or Firm* — Tarolli, Sundheim, Covell & Tummino LLP

(57) ABSTRACT

A mechanical tracking system comprises a first set of linkage arms, a second set of linkage arms, a pair of shafts connected at a first end to one arm of the first set of linkage arms and at a second end to one arm of said second set of the linkage arms, wherein each arm of the second set of linkage arms is oriented out of phase with a respective arm of the first set of linkage arms, an attachment shaft positioned adjacent to the first set of linkage arms to accommodate a tool, and a sensor arrangement configured to sense the orientation and position of the attachment shaft.

21 Claims, 15 Drawing Sheets

(51) Int. Cl.
*G01D 5/14* (2006.01)
*G01B 5/004* (2006.01)
*A61B 6/03* (2006.01)
*A61B 8/08* (2006.01)
*A61B 8/00* (2006.01)
*A61B 5/055* (2006.01)
*G01D 5/26* (2006.01)
*A61B 34/20* (2016.01)
*A61B 90/11* (2016.01)
*A61B 34/30* (2016.01)
*A61B 90/00* (2016.01)

(52) U.S. Cl.
CPC .......... *A61B 8/0841* (2013.01); *A61B 8/0858* (2013.01); *A61B 8/4218* (2013.01); *A61B 8/483* (2013.01); *A61B 34/20* (2016.02); *A61B 90/11* (2016.02); *G01B 5/004* (2013.01); *G01D 5/26* (2013.01); *A61B 8/4263* (2013.01); *A61B 8/466* (2013.01); *A61B 34/30* (2016.02); *A61B 2034/2059* (2016.02); *A61B 2090/378* (2016.02)

(58) Field of Classification Search
CPC ....... A61B 6/032; A61B 8/0841; A61B 8/085; A61B 5/055; A61B 8/0858; A61B 34/30; A61B 2034/2059; A61B 2090/378; A61B 8/466; A61B 8/4263; G01B 5/004
USPC ................................ 324/207.25, 252, 207.11
See application file for complete search history.

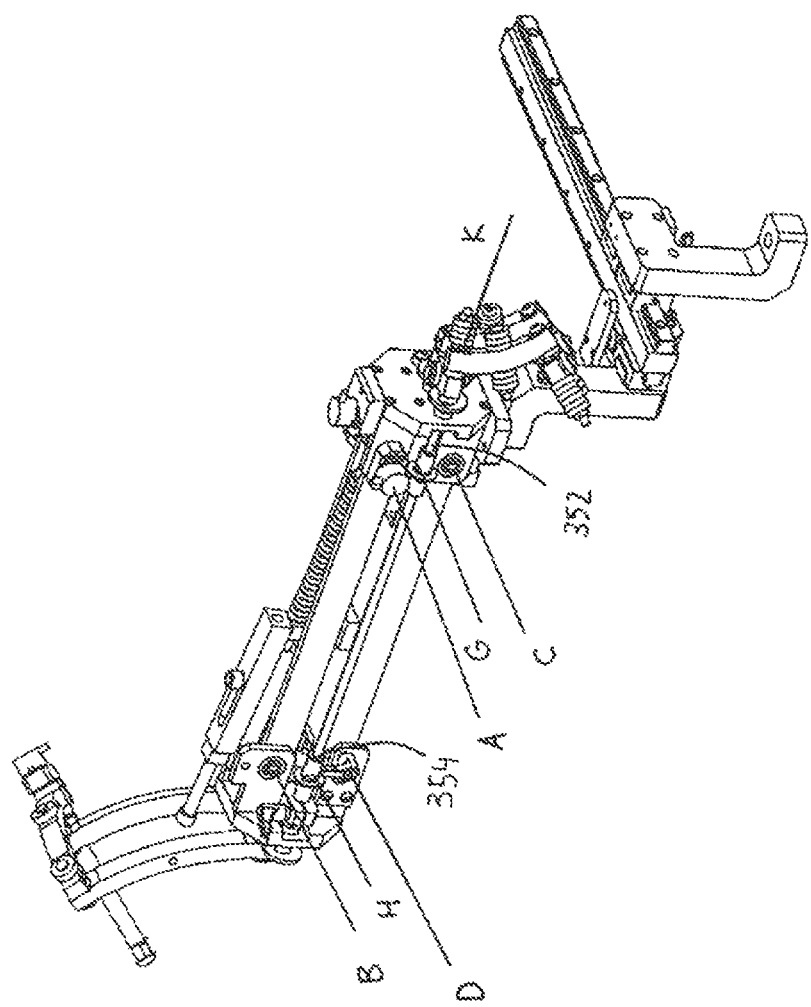

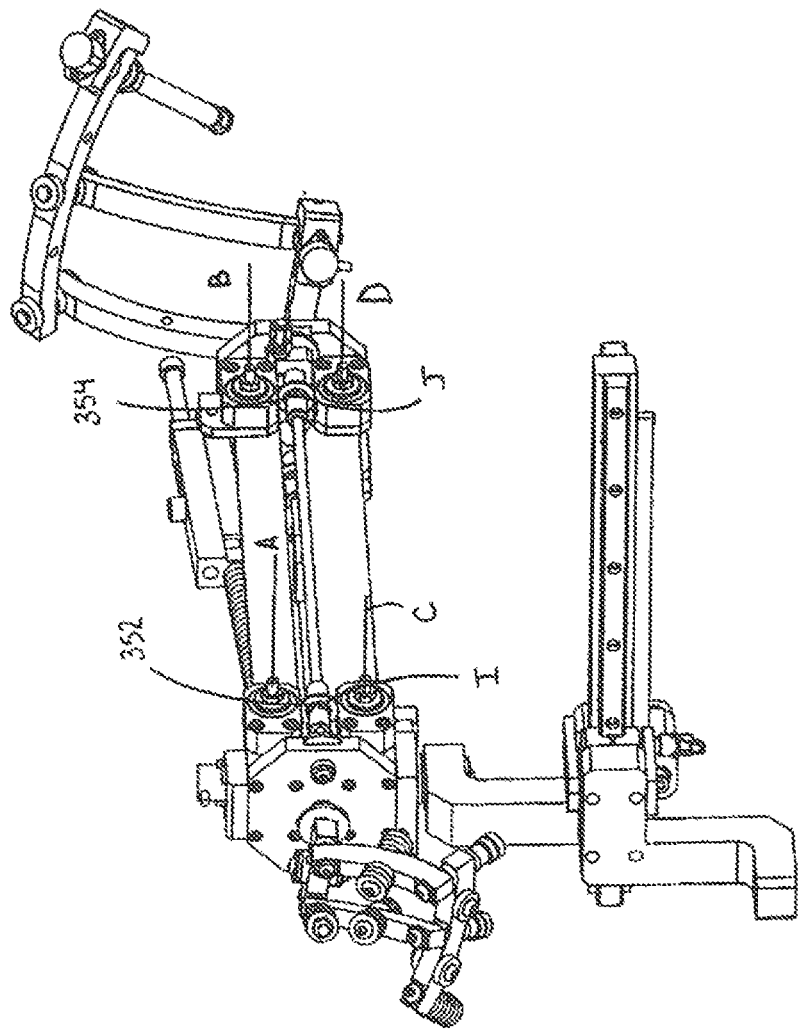

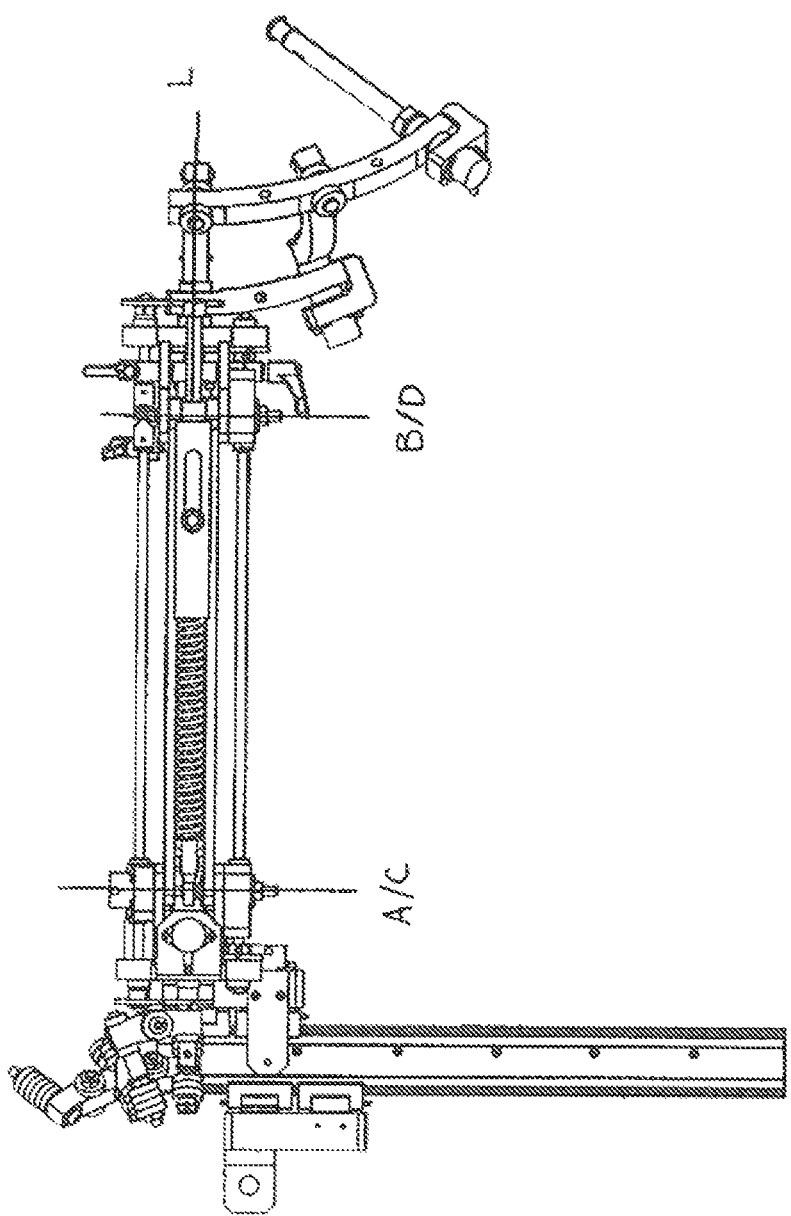

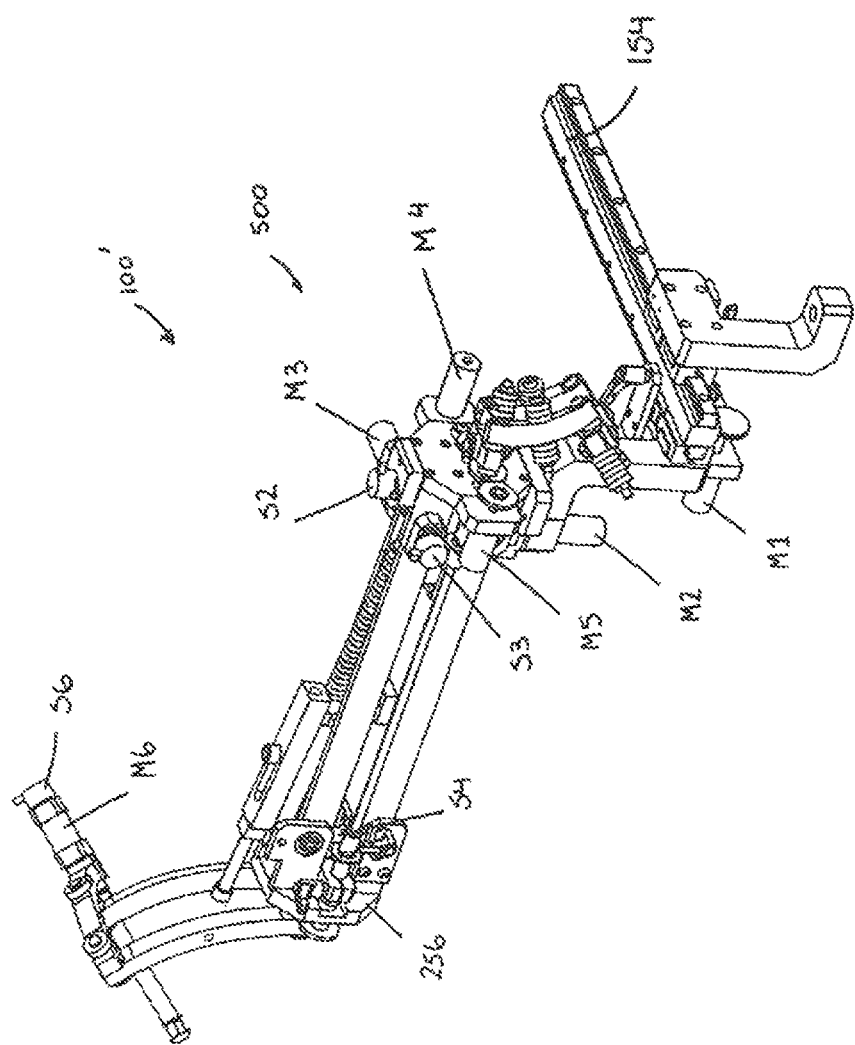

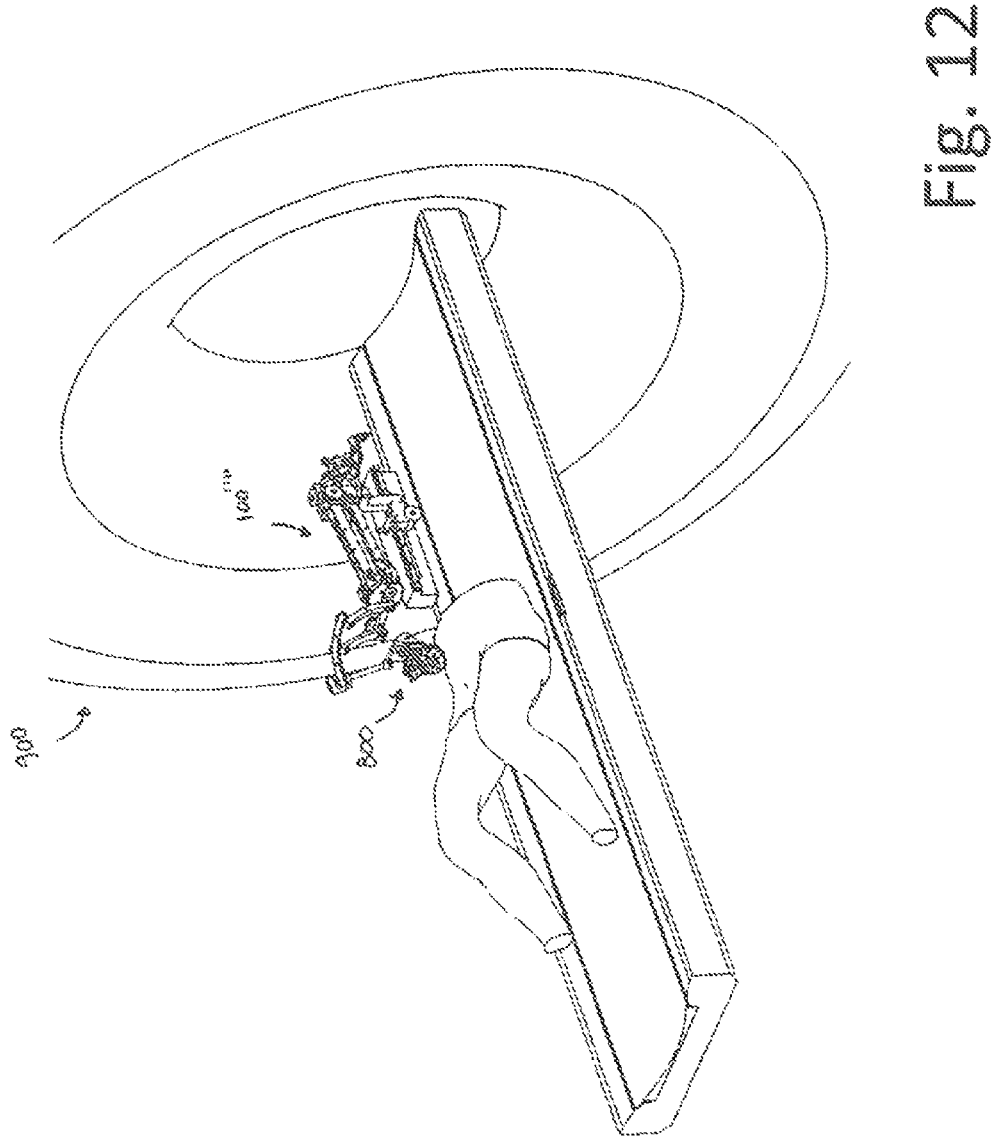

MECHANICAL TRACKING SYSTEM

CROSS-REFERENCE TO RELATED APPLICATION

This application claims the benefit of U.S. Provisional Application No. 61/671,701 to Jeffrey Bax et al. filed on Jul. 14, 2012, the entire content of which is incorporated herein by reference.

FIELD OF THE INVENTION

The present invention relates to tracking systems and in particular to a mechanical tracking system to assist in medical imaging.

BACKGROUND OF THE INVENTION

Hepatocellular carcinoma (HCC) is one of the most common diagnosed malignancies and one of the most frequent causes of cancer related deaths worldwide. Incidence is particularly high in Asia and Sub-Saharan Africa due to the large incidence of hepatitis B and C, both of which are complicated by hepatic cirrhosis, the greatest risk factor for HCC. Increasing trends in HCC have been reported in Western countries. Further, the liver is one of the most common sites of metastatic cancer arising in other organs.

When feasible, surgical resection or liver transplant is the accepted standard therapeutic approach, and has the highest success rate of available treatment methods for primary and metastatic liver cancer. Unfortunately, only approximately 15% of patients are candidates the surgery. Patients who do not qualify for surgery are offered other therapeutic solutions such as for example chemotherapy and radiotherapy, however these other solutions have variable success rates.

Minimally invasive percutaneous techniques, such as for example radio-frequency (RF) and microwave (MW) ablation of malignant tissue in the liver is a rapidly expanding research field and treatment tool for patients who are not candidates for surgical resection or liver transplant. In some cases, these minimally invasive percutaneous techniques act as a bridge to liver transplantation. Due to low complication rates and short recovery times, the indications for these minimally invasive techniques are increasing. These techniques, however, have a higher local recurrence rate than surgical resection mainly due to insufficient or inaccurate local ablation of cancerous cells.

MW energy-induced tissue heating by near field probes is a common thermal treatment of liver tumours. Application of MW for tumour ablation has multiple advantages over other techniques, including higher treatment temperatures and the ability to create larger uniformly shaped ablation zones in shorter time periods. However, the accurate placement of the ablation probe is critical in achieving the predicted treatment goal. The current standard uses computed tomography (CT) images for planning and two-dimensional ultrasound image guidance for intra-operative guidance of the ablation probe(s) into the target lesion. This approach suffers from several disadvantages such as: (1) 2D ultrasound imaging requires users (physicians) to mentally integrate a sequence of 2D images to form an impression of the anatomy and pathology, leading to variability in guidance during interventional procedures; (2) 2D ultrasound imaging does not permit the viewing of planes parallel to the skin; (3) liver deformation and motion artifact due to breathing reduces targeting accuracy; (4) the use of 2D ultrasound imaging for measurement of tumour volume needed for the treatment plan is variable and at times inaccurate and (5) the use of 2D ultrasound imaging makes it difficult to detect and track the needle delivering the thermal energy to the liver, which is crucial for accurate placement of the needle relative to the tumour.

The use a three-dimensional (3D) ultrasound imaging helps to overcome the above-noted disadvantages resulting in improved accuracy of ablation probe placement and improved ablation of the lesion. 3D ultrasound imaging also helps to show the features of liver masses and the hepatic vasculature more clearly, allowing guidance of the ablation probe to the target to be carried out more accurately and allowing more accurate monitoring of the ablation zone during the procedure and during follow up. As a result, 3D ultrasound imaging helps to increase the overall success rate and reliability of minimally invasive liver interventions. Thus, 3D ultrasound in combination with follow up CT images can help physicians to decide whether a repeat ablation is required.

The ability to increase the overall success rate of minimally invasive techniques for the treatment of liver cancer provides better treatment options for non-surgical candidates. It is them fore an object of the present invention at least to provide a novel mechanical tracking system to assist in medical imaging.

SUMMARY OF THE INVENTION

Accordingly, in one aspect there is provided a mechanical tracking system comprising a first set of linkage arms, a second set of linkage arms, a pair of shafts connected at a first end to one arm of said first set of linkage arms and at a second end to one arm of said second set of said linkage arms, wherein each arm of the second set of linkage arms is oriented out of phase with a respective arm of the first set of linkage arms, an attachment shall positioned adjacent to the first set of linkage arms to accommodate a tool, and a sensor arrangement configured to sense the orientation and position of the attachment shaft.

In one embodiment, the first and second sets of linkage arms are 180° out of phase with respect to one another and form spherical packages. The spherical linkages are coupled to opposite ends of a parallelogram linkage. The first set of linkage arms and parallelogram linkage are coupled to a linear slide assembly.

In one embodiment, the sensor arrangement comprises at least one encoder. The at least one encoder may be a magnetic encoder and an optical encoder. In another embodiment, the sensor arrangement comprises a plurality of sensors at different locations about the mechanical tracking system.

In one embodiment, the mechanical tracking system further comprises a counterbalance mechanism for maintaining balance between the first and second set of linkage arms. The counterbalance mechanism may comprise counterweights mounted on the first set of linkage arms.

According to another aspect there is provided an assembly comprising a parallelogram linkage; a first spherical linkage coupled to one end of the parallelogram linkage and being configured to connect to a tool; a second spherical linkage coupled to an opposite end of the parallelogram linkage; and a counterbalance mechanism separated from said first spherical linkage.

In one embodiment, the first and second spherical linkages are mirrored at opposite ends of the parallelogram linkage and the counterbalance mechanism is associated with the second spherical linkage. The counterbalance mechanism may comprise counterweights mounted on linkage arms of said second spherical linkage. In one embodiment, the assembly further comprises a shaft and U-joint arrangement extending between the first and second spherical linkages and the parallelogram linkage and second spherical linkage are coupled to a linear slide assembly.

The mechanical tracking assembly is advantageous in that it allows for both spherical and vertical counterbalanced motion and reduced inertia.

BRIEF DESCRIPTION OF THE DRAWINGS

Embodiments will now be described more fully with reference to the accompanying drawings in which:

FIGS. 4a to -4c are front perspective, rear perspective, and top views, respectively, of the mechanical tracking system of FIG. 1;

FIG. 9a and 9b are isometric and side views, respectively, of another embodiment of a mechanical tracking system;

FIG. 12 is an isometric view of still yet another embodiment of a mechanical tracking system coupled to a magnetic resonance imaging machine.

DETAILED DESCRIPTION OF THE EMBODIMENTS

Figure 1:
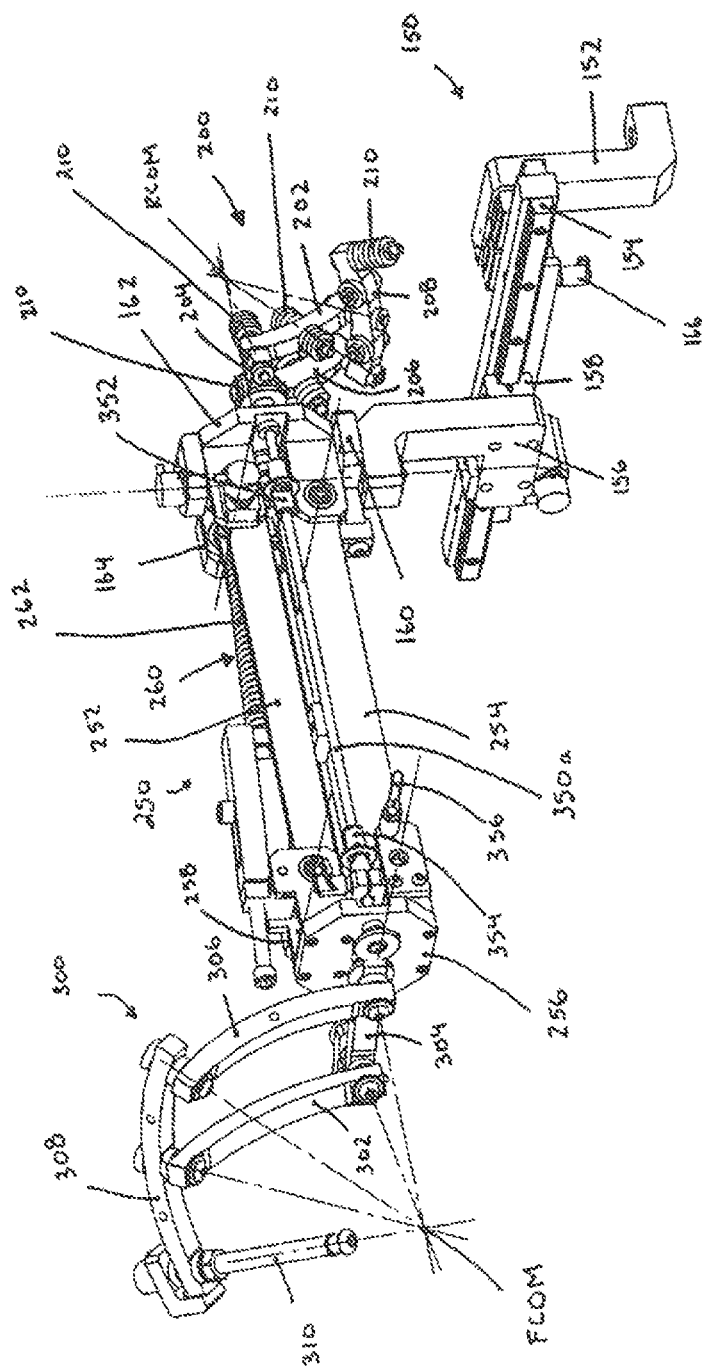
FIG. 1 is an isometric view of a mechanical tracking system.
Figure 2:
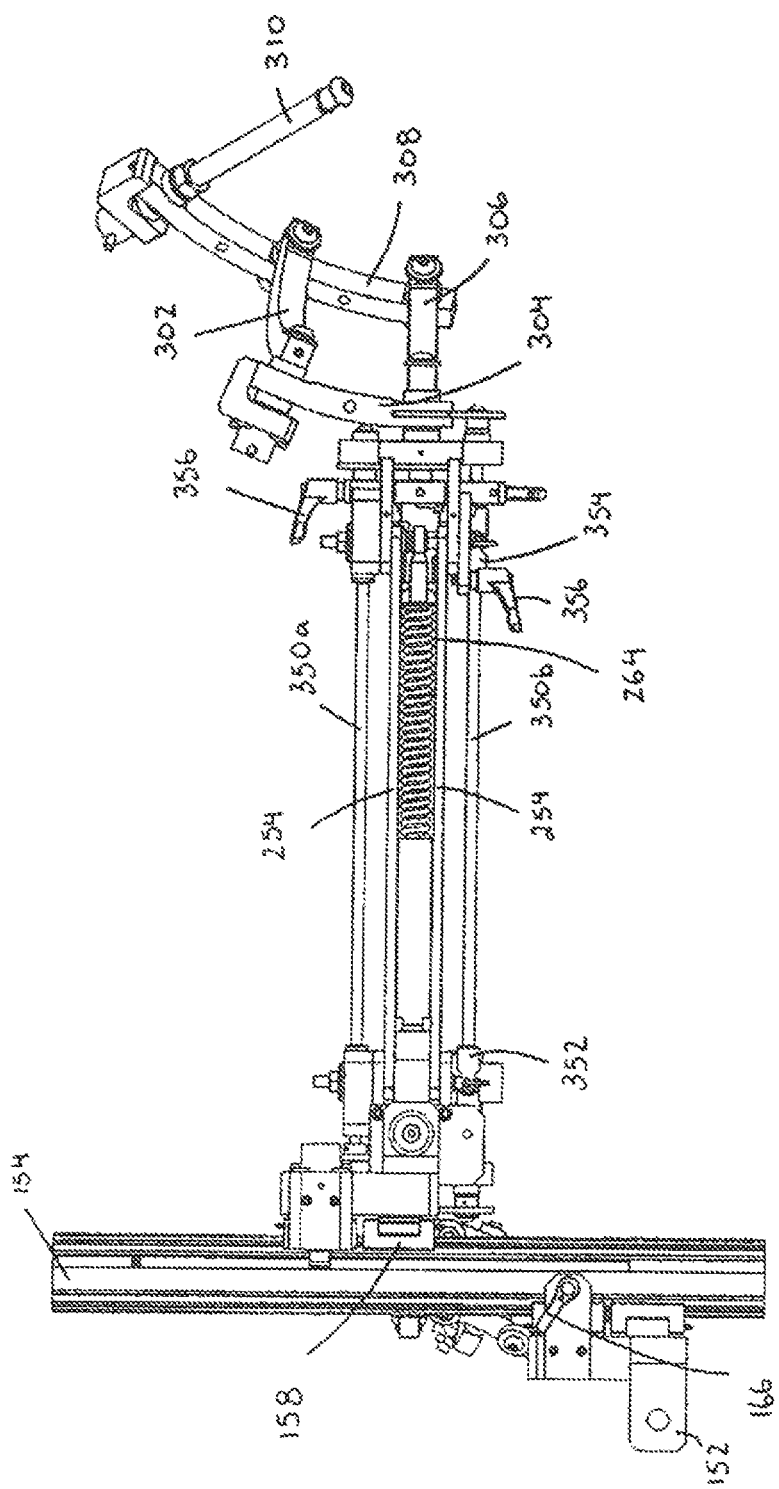
FIG. 2 is a bottom view of the mechanical tracking system of FIG. 1.

Tuning to FIGS. 1 and 2, a mechanical tracking system is shown and is generally identified by reference numeral 100. The mechanical tracking system 100 comprises a linear sliding assembly 150, a rearward spherical linkage 200, an arm assembly 250, a spring counterbalance assembly 260 and a forward spherical linkage 300. The forward spherical linkage 300 comprises an attachment shaft 310 for connecting to a tool such as for example a medical imaging device (e.g. an ultrasound probe CT scanner, MR scanner etc.). The mechanical tracking system 100 also comprises a sensor arrangement 400 for monitoring the motion thereof.

The linear sliding assembly 150 comprises a first base bracket 152 having one end configured to be secured or otherwise mounted on supporting structure. A horizontally extending linear carriage 154 is mounted adjacent the other end of the first base bracket. A bottom portion of a second base bracket 156 is slidably connected to the linear carriage 154 via a linear slide 158. A brake 166 is provided to selectively inhibit or permit movement of the linear slide 158 along the linear carriage 154. A top portion of the second base bracket 156 is connected to a yaw bearing block 160.

The yaw bearing block 160 supports a rear base plate 162. A first pitch bearing block 164 is connected to the rear base plate 162. Although not visible in FIG. 1, a second pitch bearing block is connected to the rear base plate 162 below the first pitch bearing block 164.

The rearward spherical linkage 200 extends rearwardly from the rear base plate 162 and comprises four (4) spherical linkage arms 202 to 208, which in this embodiment are made of aluminum or other suitable material. The spherical linkage arms 202 to 208 are arranged in a generally rectangular shape and are connected to one another via a pair of stainless steel bearings that are seethed by a threaded screw and a bolt (not shown). Specifically, a first end of each of spherical linkage arms 202 and 206 is connected to opposing ends of spherical linkage arm 204. A second end of spherical linkage arm 206 is connected to a first end of spherical linkage arm 208 and a second end of spherical linkage arm 202 is connected to an approximate midpoint of spherical linkage arm 208. The second end of spherical linkage arm 208 extends generally outward from the connection point of the second end of spherical linkage arm 202. Counterweights 210 formed of tungsten or other suitable material are positioned approximately at the midpoints of spherical linkage arms 202, 204 and 206, at the connection point between the first end of spherical linkage arm 202 and spherical linkage arm 204, and at the second end of spherical linkage arm 208. As will be further described below, the rearward spherical linkage 200 is used to counterbalance the mass of the forward spherical linkage 300 and tool connected thereto via attachment shaft 310.

The arm assembly 250 extends forwardly from the rear base plate 162 and is in the form of a parallelogram linkage that comprises an upper parallelogram linkage arm 252 and a lower parallelogram linkage arm 254, respectively. In this embodiment, each of the upper and lower parallelogram linkage arms 252 and 254 is U-shaped and is connected at a first end to the rear base plate 162 via is pair of stainless steel bearings associated with the first pitch bearing block 164 and second pitch bearing block (not shown), and at a second end to a forward base plate 256 via a pair of stainless steel bearings associated with a third pitch bearing block 258 and a fourth pitch bearing block (not shown). Positioned within a space intermediate the upper parallelogram linkage arm 252 and the lower parallelogram linkage arm 254 is the spring counterbalance assembly 260. The spring counterbalance assembly 260 is similar to that described in International PCT Application Publication No. WO 2009/039659 to Bax et al., the relevant portions of the disclosure of which are incorporated herein by reference.

Figure 3:
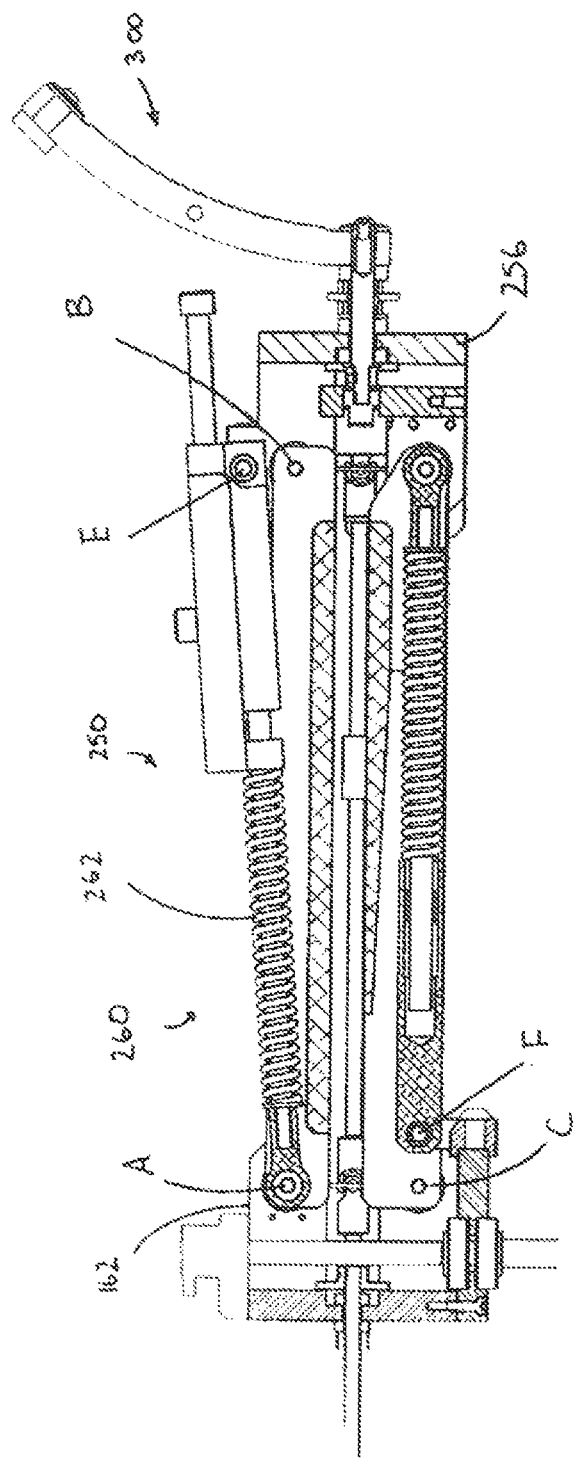
FIG. 3 is a cross-sectional view of the mechanical tracking system of FIG. 1.

FIG. 3 shows a cross-sectional view of the mechanical tracking system 100. Generally, the spring counterbalance assembly 260 is used to support the mass of the arm assembly 250, forward spherical linkage 300 and tool connected to the attachment shaft 310 and comprises an upper counterbalance spring 262 connected at a first end to the rear base plate 162, identified as point A in FIG. 3, and at a second end to a first end of an upper crank BE via a pinned connection E, which itself is connected to the forward base plate 256. The spring counterbalance assembly 260 comprises a lower counterbalance spring 264 connected at a first end to the rear base plate 162, identified as point C in FIG. 3, and at a second end to a first end of a lower crank CF via a pinned connection F. The second end of the lower crank CF is connected to the forward base plate 256 at point D. As will be appreciated from this arrangement, the force generated by the upper counterbalance spring 262 is 90 degrees out of phase with respect to the lower counterbalance spring 264 and upper crank BE is at a right angle with respect to lower crank CF. In this embodiment the upper and lower counterbalance springs 262 and 264 are steel alloy springs.

Referring back to FIGS. 1 and 2, the forward spherical linkage 300 extends forwardly from the forward base plate 256 and comprises four (4) spherical linkage arms 302 to 308, which in this embodiment are made from aluminum or other suitable materials. The spherical linkage arms 302 to 308 are arranged in a generally rectangular shape and are connected to one another via a pair of stainless steel bearings that are secured by a threaded screw and a bolt (not shown). Specifically, a first end of each of spherical linkage arms 302 and 306 is connected to opposing ends of spherical linkage arm 304. A second end of spherical linkage arm 306 is connected to a first end of spherical linkage arm 308 and a second end of spherical linkage arm 302 is connected to an approximate midpoint of spherical linkage arm 308. The second end of spherical linkage arm 308 extends generally outward from the connection point of the second end of spherical linkage arm 302. The second end of spherical linkage arm 308 houses the attachment shaft 310. The attachment shaft 310 extends generally inwards and is moveable with the spherical linkage arms 302 to 308, as will be described.

As can be seen, spherical linkage arms 202, 204, 206 and 208 correspond to spherical linkage arms 302, 304, 306 and 308, respectively and thus, the rear and forward spherical linkages 200 and 300 are mirrored at opposite ends of the parallelogram linkage. The rearward spherical linkage 200 and forward spherical linkage 300 are coupled to one another via shaft and U-joint arrangements. The shafts 350a and 350b of the arrangements in this embodiment are parallel and are made of stainless steel or other suitable material. The rearward spherical linkage 200 is connected to a first end of each of the shafts 350a and 350b via a pair of U-joints 352. Each pair of U-joints 352 is connected to one another such that they are 90° out of phase with respect to one another. The forward spherical linkage 300 is connected to a second end of each of the shafts 350a and 350b via a pair of U-joints 354. Each pair of U-joints 354 is connected to one another such that they at 90° out of phase with respect to one another. As a result, the rearward spherical linkage 200 and forward spherical linkage 300 are positioned 180° out of phase with respect to one another, that is, spherical linkage arms 202, 204, 206 and 208 are 180° out of phase with respect to spherical linkage arms 302, 304, 306 and 308, respectively.

FIGS. 4a to 4c are respective front perspective, rear perspective, and top views of the mechanical tracking system 100 showing the relationship between the U-joints 352 and 354 and the pivot axes of the upper parallelogram linkage arm 252, lower parallelogram linkage arm 254, forward spherical linkage 300 and rearward spherical linkage 200. As can be seen, the center of rotation of each pair of U-joints 352 and 354 is aligned with the pivots adjacent to the respective forward spherical linkage 300 (points G and I which are coplanar with respect to the plane defined by parallel axes A and C) or rearward spherical linkage 200 (points H and J which are coplanar with respect to the plane defined by parallel axes B and D) such that all four pairs of U-joints are parallel to the pinned axis supporting the forward spherical linkage 300 (axis L) and rearward spherical linkage 200 (axis K).

Figure 5:
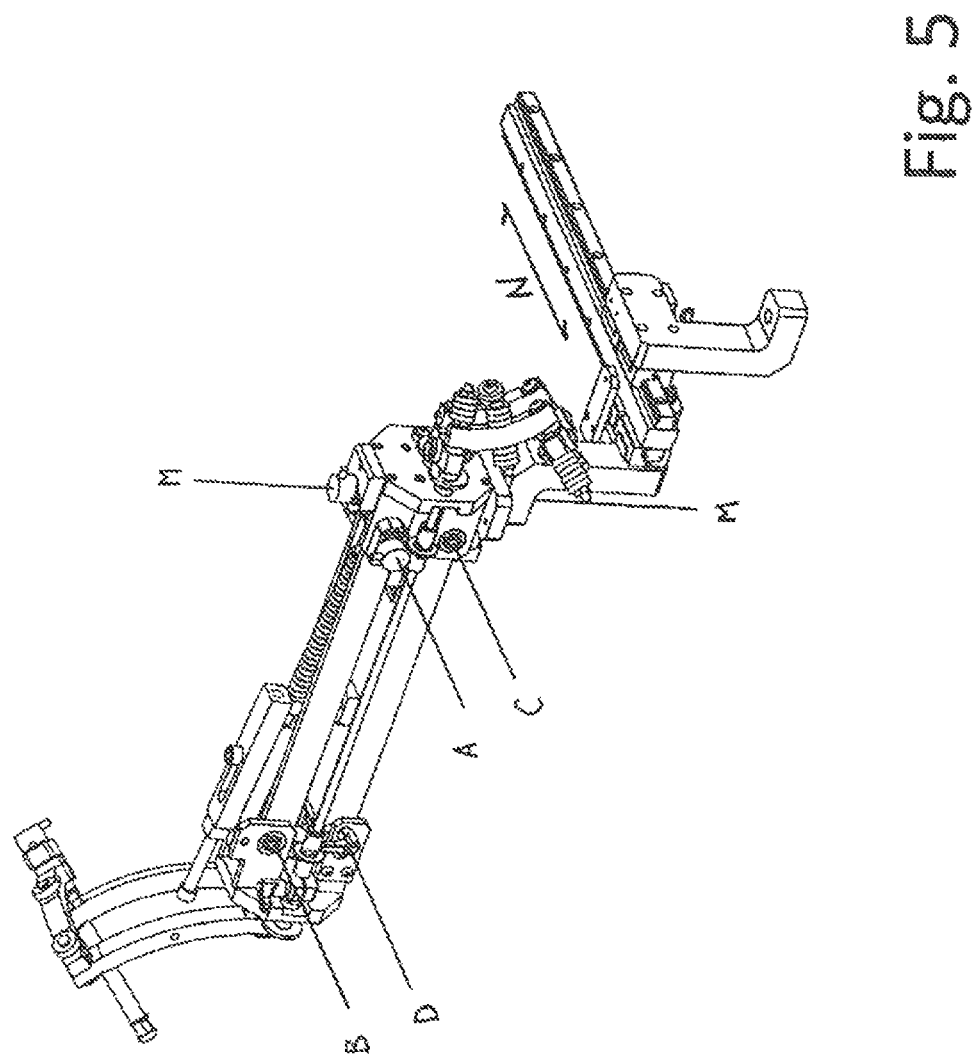
FIG. 5 is an isometric view of the mechanical tracking system of FIG. 1 showing axes of movement thereof.

As best shown in FIG. 1, the rearward spherical linkage 200 is rotatable about a rear center of motion RCOM and the forward spherical linkage 300 is rotatable about a forward center of motion FCOM. The forward spherical linkage 300 permits a user to pivot a tool attached to attachment shaft 310 about the forward center of motion FCOM with three degrees of rotation; namely yaw, pitch and roll. The arm assembly 250 which is pinned to the second base bracket 156 that is attached to the linear sliding assembly 150 permits three degrees of translation to adjust the position (X, Y, Z) of the forward center of motion FCOM and the tool attached to the attachment shaft 310. As will be appreciated, the three degrees of translation is provided through a combination of the up/down movement of the parallelogram linkage about axes ABCD shown in FIG. 5, the pivoting of the parallelogram linkage about axis M, and the translation along the linear sliding assembly 150 according to direction N. A pair of brakes 356 (shown in FIG. 1) is provided to selectively inhibit or permit rotation of the forward spherical linkage 300 and rearward spherical linkage 200.

Figure 6:
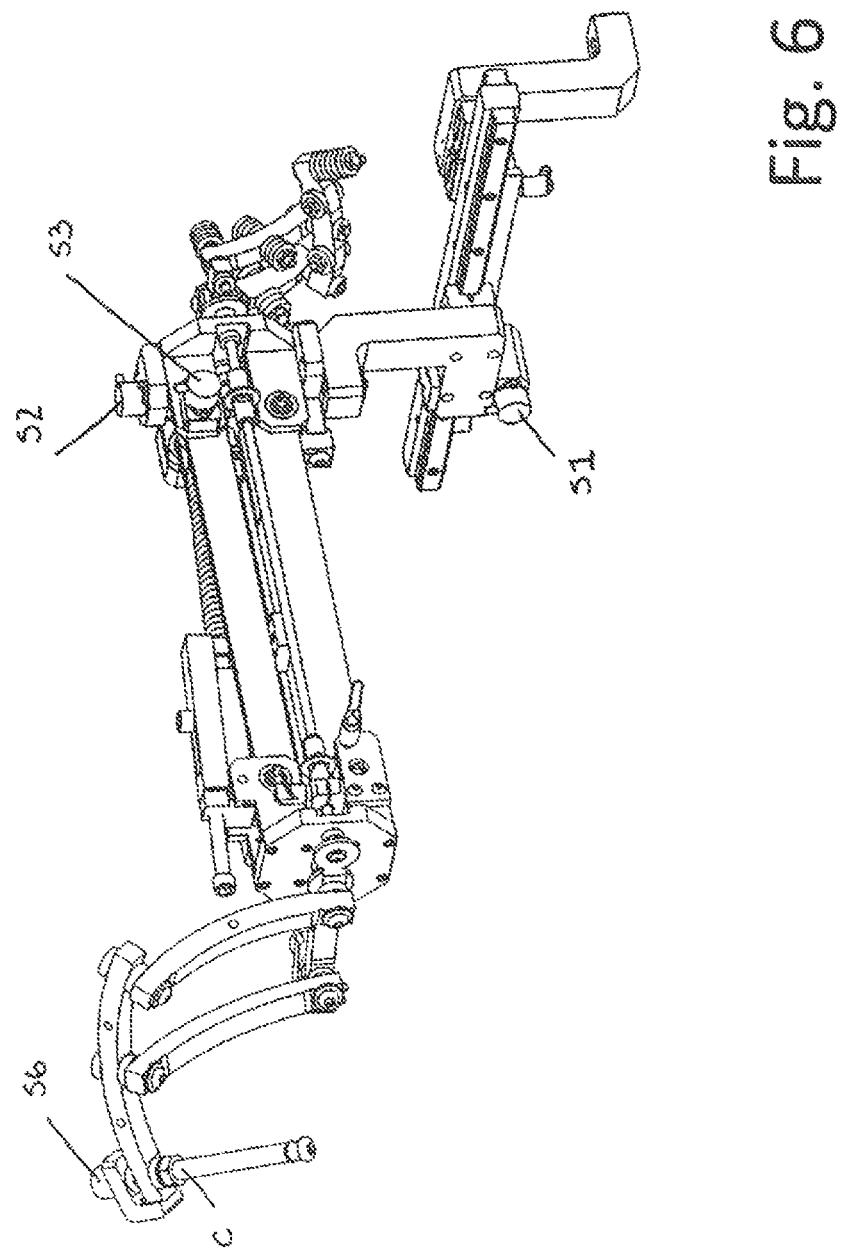
FIG. 6 is an isometric view of the mechanical tracking system of FIG. 1 showing a sensor assembly thereof.
Figure 7:
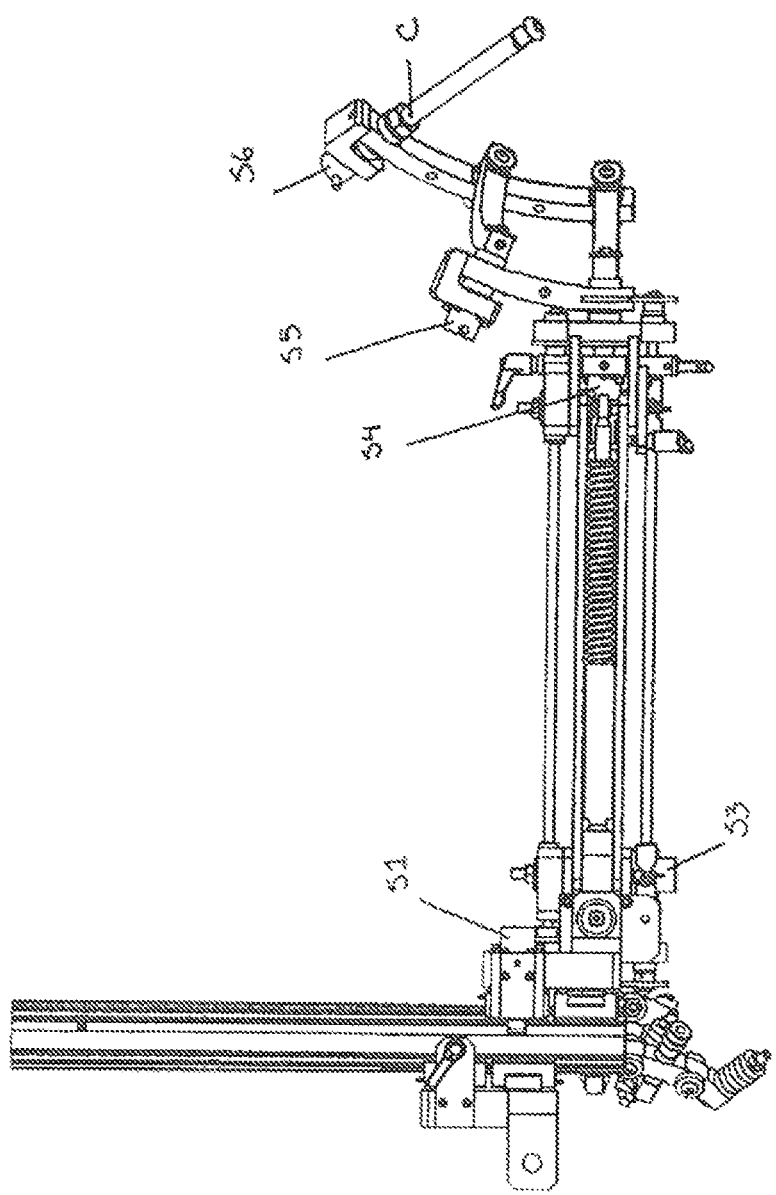
FIG. 7 is a bottom view of the mechanical tracking system of FIG. 1 showing the sensor assembly thereof.

The position of the tool attached to attachment shaft 310 is tracked by the sensor arrangement 400 relative to a fixed coordinate frame. The sensor arrangement 400 is identified in FIGS. 6 and 7. As can be seen, the sensor arrangement 400 comprises six (6) encoders S1 to S6. In this embodiment, each of the six encoders S1 to S6 is a magnetic rotary encoder, such as the RM Series Rotary Encoder manufactured by Renishaw, and is used to measure the angle between the encoder body (identified as S1 to S6) and an associated encoder magnet (not shown). Each of the encoders S1 to S6 is connected to a general purpose computing deice via a wired or wireless connection (not shown). Encoder S1 is positioned on the second base bracket 156. Encoder S2 is positioned atop rear base plate 162. Encoder S3 is positioned on an exterior side of upper parallelogram linkage arm 252. Encoder S4 is positioned behind the forward base plate 256. Encoder S5 is positioned behind the connection point of spherical linkage arms 302 and 304. Encoder S6 is positioned behind attachment shaft 310 on spherical linkage arm 308.

Figure 8:
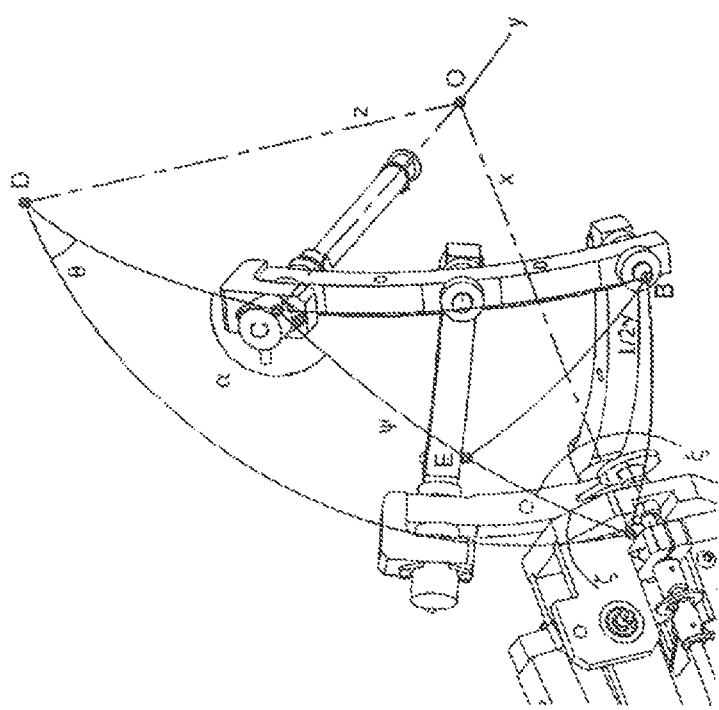
FIG. 8 is a schematic diagram showing the relationship between the coordinate system of the mechanical tracking system and a reference frame.

Referring to FIG. 8, the position of the tool is determined by calculating the forward center of motion FCOM position, having coordinates (X, Y, Z) relative to a known starting point using data obtained by encoders S1, S2 and S3 and the following transformation matrix:

$$\begin{bmatrix} \cos A & \sin A & 0 & x_4\cos A + x_3\cos A\cos B + x_2\cos A + x_1 \\ -\sin A & \cos A & 0 & -x_4\sin A - x_3\sin A\cos B - x_2\sin A \\ 0 & 0 & 1 & -x_3\sin B + z_1 \\ 0 & 0 & 0 & 1 \end{bmatrix} \quad [1]$$

where $x_1$, $x_2$, $x_3$ and $x_4$ are constants determined from the geometry of the forward spherical linkage 300, $z_1$ is the displacement along the linear carriage 154 measured by encoder S1, angle A is the yaw angle measured by encoders S2 and S3, and angle B is the pitch angle measured by encoders S2 and S3.

The orientation of the tool is determined by calculating the orientation of point C using data obtained by encoders S4, S5 and S6. The orientation of the tool about the axis from the forward center of motion ECOM to point C, referred to as axis FCOM-C, is measured by encoder S6. The location of point C with respect to the forward center of motion FCOM is measured by encoders S4 and S5. The orientation of the tool is specified in spherical coordinates by the angle φ, the angle axis FCOM-C makes with respect to the z axis, and the angle θ representing the orientation of the tool in the x-y plane.

The relationship between the coordinate system of the mechanical tracking system 100 and the reference frame defined by the encoders S1 to S6 is shown in FIG. 8. The attachment shaft 310 orientation measured by the encoders S4 to S6 is defined by the spherical triangle ABC, and is linked to the forward center of motion FCOM by the spherical triangle ADC. The angle between joints A and B in link AB is $\pi/4$. Similarly, the angle between joints B and C in link BC is $\pi/4$.

The kinematics equations of motion for the forward spherical linkage 300 derived by applying the Napier analogies to spherical triangle ADC shown in FIG. 8 are:

$$\tan\frac{1}{2}(\theta + \alpha) = \cos\frac{1}{2}(\psi - \frac{\pi}{2})\sec\frac{1}{2}(\psi + \frac{\pi}{2})\cot\frac{1}{2}\zeta \quad [2a]$$

$$\tan\frac{1}{2}(\theta - \alpha) = \sin\frac{1}{2}(\psi - \frac{\pi}{2})\csc\frac{1}{2}(\psi + \frac{\pi}{2})\cot\frac{1}{2}\zeta \quad [2b]$$

$$\tan\frac{1}{2}\varphi = \tan\frac{1}{2}(\psi - \frac{\pi}{2})\sin(\theta + \alpha)\cos(\theta - \alpha) \quad [2c]$$

As will be appreciated, Equations 2a to 2c are used to define the spherical coordinates of axis FCOM-C in terms of the geometric configuration of the linkage angles $\psi$ and $\zeta$.

The configuration of the forward spherical linkage 300 in terms of the angles measured by encoders S4 and S5 is defined according to Equations 3a and 3b below. It will be appreciated that Equations 3a and 3b are derived by solving the right spherical triangle ABE in FIG. 8:

$$\tan\frac{1}{2}\psi = \cos\xi \quad [3a]$$

$$\cot\frac{1}{2}\psi = \frac{1}{\sqrt{2}}\tan\gamma \quad [3b]$$

The positions of spherical linkage arms 306 and 308 of forward spherical linkage 300 correspond to arms AB and BC, respectively. Accordingly, the position of each spherical linkage arm 306 and 308 is determined by measuring the spherical angles at each of the pinned couplings A and B, respectively. Encoder S4 measures the angle $(\xi+\zeta)$ between arm AB and the x-Z plane, and encoder S5 measures the angle $\gamma$ between arm AB and arm BC. As will be appreciated, Equations 3a and 3b are used to decouple the values for angles $\xi$ and $\gamma$, which in turn are used to solve Equations 2a to 2e, above.

During operation, the general purpose computing, device (not shown) polls the encoders S1 to S6 to obtain coordinates therefrom in this embodiment, the general purpose computing device polls each encoder S1 to S6 at a one of 10 polls per second. The general purpose computing device processes the coordinates and displays the coordinates of the tool attached to the attachment shaft 310. In embodiments where the tool is a medical imaging device, the general purpose computing device may superimpose the coordinates or tool path of the medical imaging device on a display screen atop a reconstructed image such as for example an ultrasound image, a computed tomography (CT) image, or a magnetic resonance (MR) image. Further, if the tool is a CT or MR imaging scanner, the mechanical tracking system may automatically register the tool to the reconstructed CT or MR image providing information about the tool location relative to the scanned anatomy.

Figure 9B:
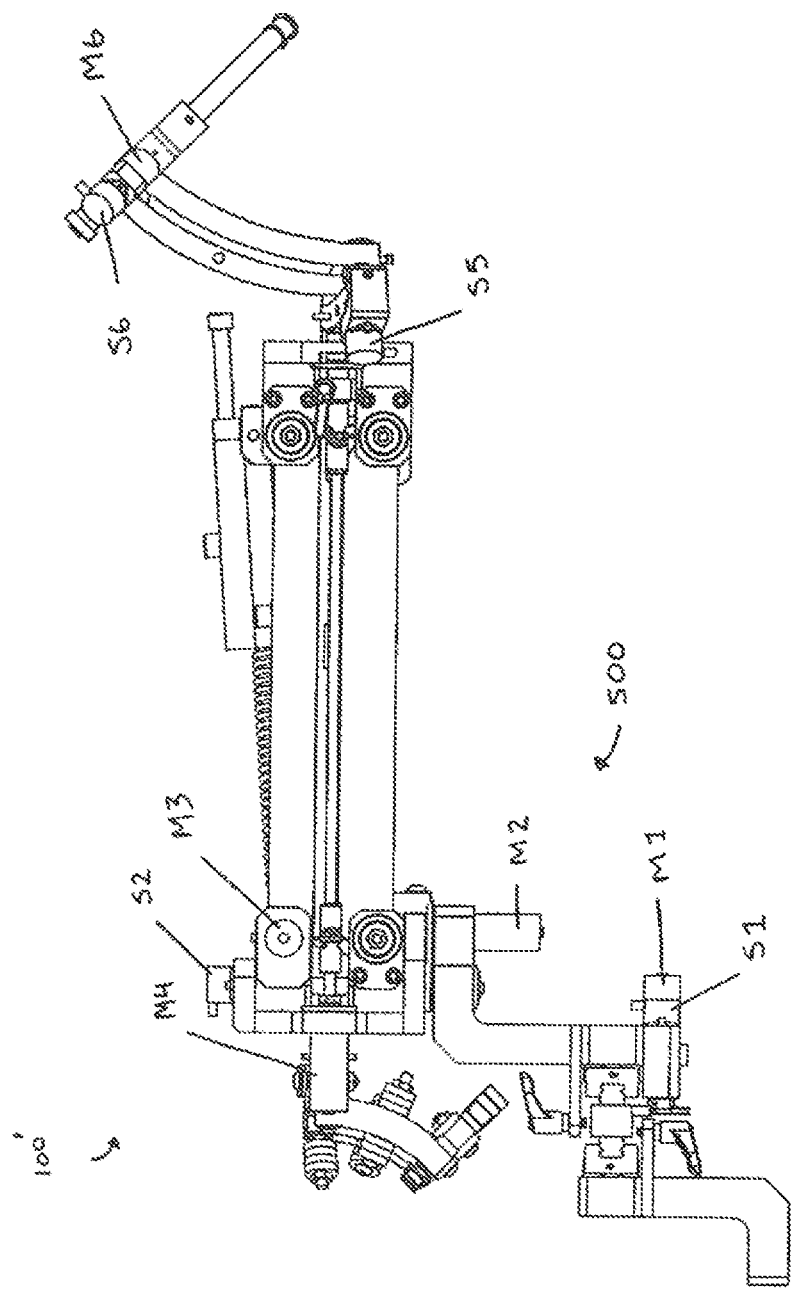

Turning now to FIGS. 9a and 9b, another embodiment of a mechanical tracking system 100' is shown. In this embodiment, like reference numerals are used to indicate like components. As can be seen, mechanical tracking system 100' is similar to that of mechanical tracking system 100 shown in FIG. 1, with the addition of a motor arrangement 500. In this embodiment, motor arrangement 500 comprises six (6) motors M1 to M6. Motor M1 controls, the movement of the arm assembly 250, rearward spherical linkage 200 and forward spherical linkage 300 along the linear carriage 154. Motor M2 controls the pivotal movement of the arm assembly 250, rearward spherical linkage 200 and forward spherical linkage 300 with respect to axis M. Motor M3 controls the up/down movement of the arm assembly 250 and forward spherical linkage 300. Motors M4 and M5 control the yaw and pitch of the tool connected to the attachment shaft 310 and are directly connected to spherical linkage arms 306 and 304, respectively. Motor M6 controls the roll orientation of the tool connected to attachment shaft 310 about the longitudinal axis thereof.

As will be appreciated, motor arrangement 500 is used as a power assist device for lifting and manipulating large payloads and/or a master-slave robotic assistant when coupled to a general purpose computing device (not shown). When used as a master-slave robotic assistant, the sensor data obtained by encoders S1 and S6 is communicated to the general purpose computing device for processing to control motors M1 to M6 and thus, adjust the position and orientation of the tool. As will be appreciated, the orientation and position of the mechanical tracking system (and thus the tool) may be adjusted through any input device such as for example a mouse, a keyboard, a tracking ball, etc.

Figure 10:
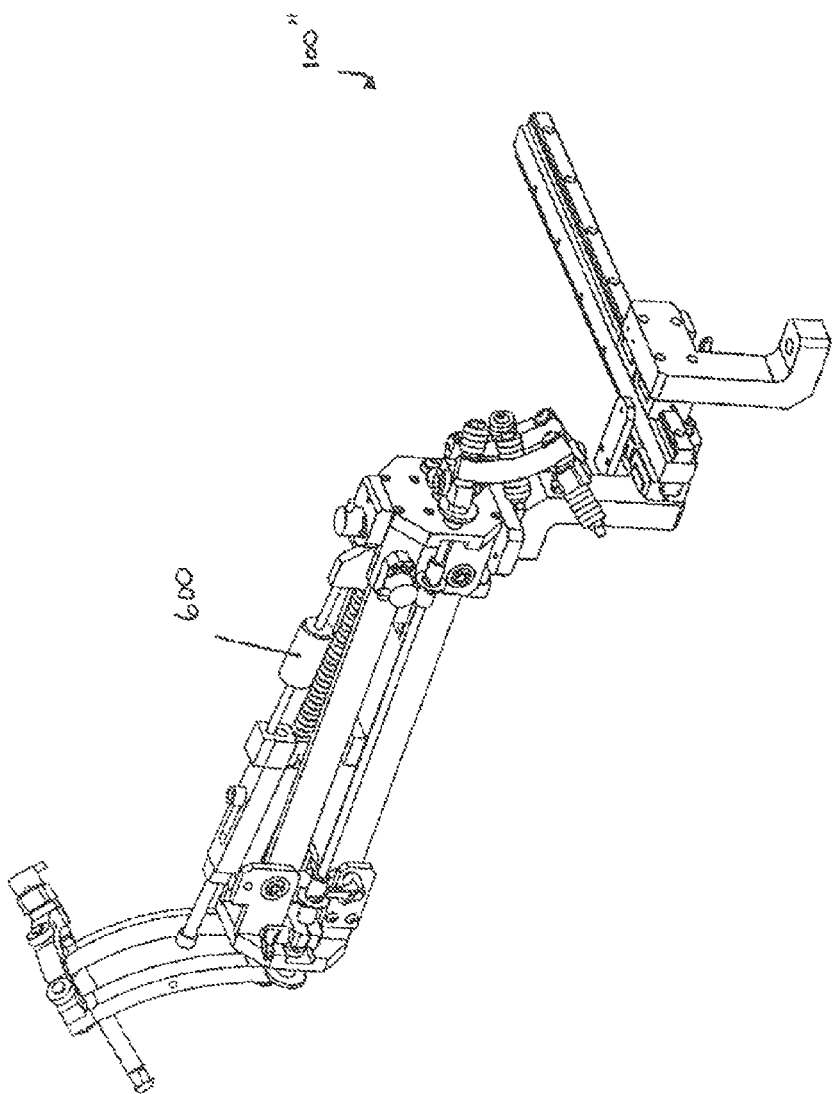
FIG. 10 is an isometric view of yet another embodiment of a mechanical tracking system.

Turning now to FIG. 10, another embodiment of a mechanical tracking system 100" is shown. In this embodiment, like reference numerals are again used to indicate like components. As can be seen, mechanical tracking system 100" is similar to that of mechanical tracking system 100' described above with reference to FIGS. 9a and 9b, with the exception that motor M3 of the motor arrangement 500 is replaced with a proportional gain solenoid 600. In this embodiment, the proportional gain solenoid 600 is integrated within the spring counterbalance assembly 260 to generate a force vector that is independent of the orientation of the arm assembly 250, rearward spherical linkage 200 and forward spherical linkage 300. The value of the force vector generated is communicated to the general purpose computing device through the spring counterbalance assembly 260 using the proportional gain solenoid 600 to provide force feedback along the vertical axis. As will be appreciated, six degrees of force feedback may be achieved by adding a solenoid assembly in place of each motor or by integrating the solenoid into the spring counterbalance assembly 260 as shown in FIG. 10. Alternatively, a solenoid can be integrated into the lower counter/balance spring 264. If integrated into the lower counterbalance spring 264, the force exerted by the solenoid on the forward spherical linkage 300 would be equivalent to exerting the same force through the center of mass of the payload, which is independent of the forward spherical linkage 300 configuration. As will be appreciated, the proportional gain solenoid 600 may be replaced with a pneumatic or hydraulic cylinder.

Although in the above embodiments, components are described as being formed of specific materials such as aluminum and stainless steel, it will be appreciated that other suitable materials may be used such as for example plastic, brass, ceramic, etc.

Although in the embodiments described above, magnetic rotary encoders are used, those skilled in the art will appreciate that non-magnetic optical encoders or other suitable sensors may be used.

Although the counterbalance springs are described above as being made of a steel ally those skilled in the an will appreciate plastic left springs or other suitable spring-like devices may be used.

Figure 11:
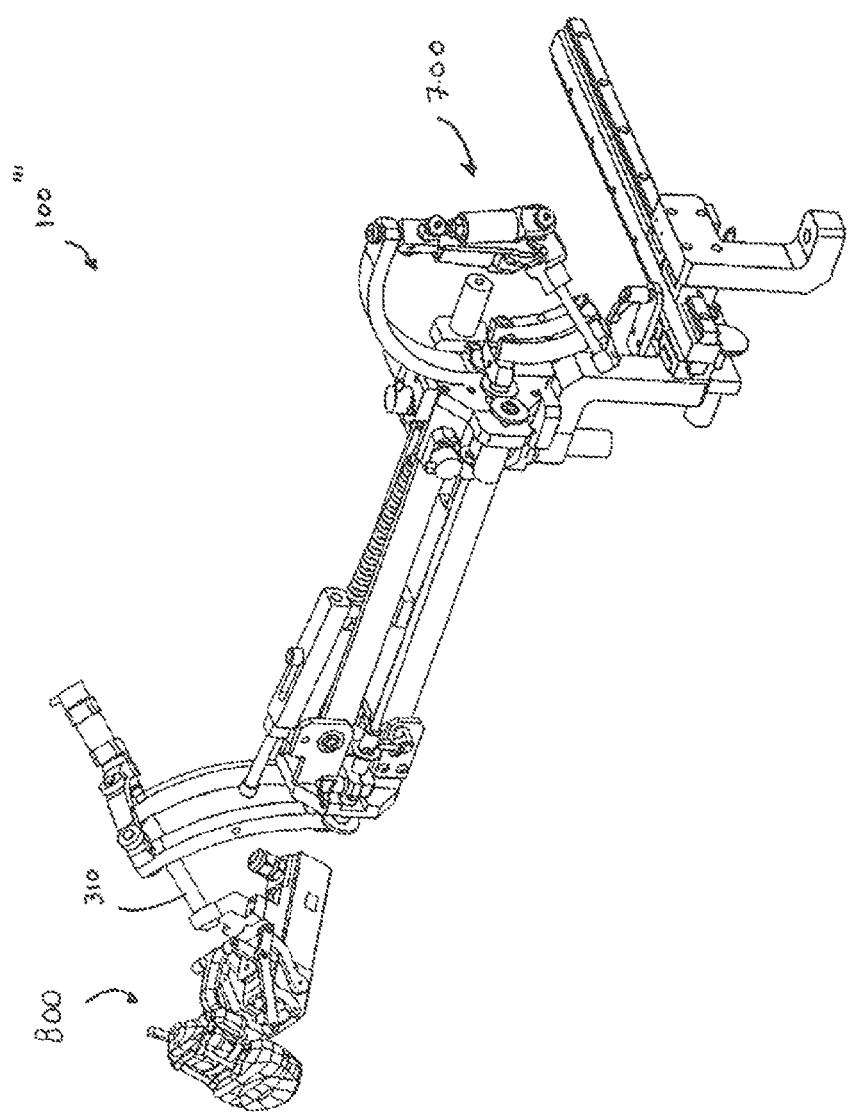
FIG. 11 is an isometric view of yet another embodiment of a mechanical tracking system holding an ultrasound imaging system.

As mentioned previously, the attachment shaft 310 may be used to connect to a medical tool. An example of the attachment shaft 310 connected to an ultrasound imaging device 800 is shown in FIG. 11. In this example, the mechanical tracking system 100''' is similar to that of mechanical tracking system 100' shown FIGS. 9a and 9b, with the exception that the tungsten counterweights 210 are replaced with a spring balance assembly 700. The spring balance assembly 700 is similar to that described in above-incorporated International PCT Application Publication No. WO 2009/039659 to Bax et al. In this example, the ultrasound imaging device 800 is similar to that described in International PCT Application No. PCT/CA2013/000302 to Barker et. al., the relevant portions of the disclosure of which are incorporated herein by reference.

FIG. 12 shows the attachment shaft 310 of mechanical tracking system 100'''' connected to an ultrasound imaging device 800 with the mechanical tracking system being mounted adjacent an MR imaging system 900. In this embodiment, it will be appreciated that all components of the mechanical tracking system 100'''' are formed of non-metallic materials so as to not interfere with the MR imaging. Specifically, the counterbalance springs are plastic leaf springs, the encoders are non-magnetic optical encoders, and all other components are made of non-metallic materials such as for example plastic, or ceramic.

Although in above embodiments, the spring counterbalance assembly comprises upper and lower cranks, in another embodiment the upper and lower cranks may be replaced with two eccentric cams positioned 90 degrees out of phase with respect to another.

Although it is described above that the position and orientation of the mechanical tracking system (and thus the tool) may be adjusted through any input device such as for example a mouse, a keyboard, a tracking ball, etc., those skilled in the art will appreciate that the position and orientation of the mechanical tracking system may be adjusted using any type of input device. For example, a scaled down model of the mechanical tracking system may be provided to a user and coupled to the general purpose computing device. In this example, the user may manipulate the sealed down model and in response, the mechanical tracking system is automatically conditioned to mirror the resultant movement of the scaled down model. As another example, a graphical user interface (GUI) maY be displayed On a display screen associated with the general purpose computing device providing a number of control buttons to the user. Further, the control buttons may be associated with a predefined movement and orientation pattern preset by the user.

Although embodiments are described above with reference to the accompanying drawings, those skilled in the art will appreciate that variations and modifications may be made without departing from the scope thereof as defined by the appended claims.

What is claimed is:

1. A mechanical tracking system comprising:
   a first set of linkage arms;
   a second set of linkage arms;
   a pair of shafts connected at a first end to one arm of said first set of linkage arms and at a second end to one arm of said second set of said linkage arms, wherein each arm of the second set of linkage arms is oriented out of phase with a respective arm of the first set of linkage arms;
   an attachment shaft positioned adjacent to the first set of linkage arms to accommodate a tool, wherein the first set of linkage arms and the second set of linkage arms are rotatable about respective first and second centers of motion (FCOM, RCOM) thereby to permit pivoting of a tool accommodated by the attachment shaft about the first center of motion with three degrees of rotation; and
   a sensor arrangement configured to sense the orientation and position of the attachment shaft.

2. The mechanical tracking system of claim 1 wherein the first and second sets of linkage arms are 180° out of phase with respect to one another.

3. The mechanical tracking system of claim 1 wherein both the first and second sets of linkage arms form spherical linkages.

4. The mechanical tracking system of claim 3 wherein the spherical linkages are coupled to opposite ends of a parallelogram linkage.

5. The mechanical tracking system of claim 4 wherein the first and second sets of linkage arms and parallelogram linkage are coupled to a linear slide assembly.

6. The mechanical tracking system of claim 3 further comprising a counterbalance mechanism for maintaining balance between the first and second sets of linkage arms.

7. The mechanical tracking system of claim 6 wherein said counterbalance mechanism comprises counterweights mounted on said first set of linkage arms.

8. The mechanical tracking system of claim 1 wherein the sensor arrangement comprises at least one encoder.

9. The mechanical tracking system of claim 8 wherein the at least one encoder is one of a magnetic encoder and an optical encoder.

10. The mechanical tracking system of claim 8 wherein the sensor arrangement comprises a plurality of sensors at different locations about the mechanical tracking system.

11. The mechanical tracking system of claim 10 wherein the sensors are encoders.

12. The mechanical tracking system of claim 1 further comprising a motor arrangement for controlling movement of the mechanical tracking system.

13. The mechanical tracking system of claim 1 comprising a pair of brakes configured to selectively inhibit or permit rotation of the first set of linkage arms about the first center of motion (FCOM) and the second set of linkage arms about the second center of motion (RCOM).

14. An assembly comprising:
   a parallelogram linkage;
   a first spherical linkage coupled to one end of the parallelogram linkage and being configured to connect to a tool;
   a second spherical linkage coupled to an opposite end of the parallelogram linkage, the second spherical linkage being 180° out of phase with respect to the first spherical linkage; and
   a counterbalance mechanism separated from said first spherical linkage,
   wherein the first and second spherical linkages are rotatable about respective first and second centers of motion (FCOM, RCOM) thereby to permit pivoting of a tool connected to the first spherical linkage about the first center of motion with three degrees of rotation.

15. The assembly of claim 14 wherein the first and second spherical linkages are mirrored at opposite ends of the parallelogram linkage.

16. The assembly of claim 15 wherein the counterbalance mechanism is associated with said second spherical linkage.

17. The assembly of claim 16 wherein the counterbalance mechanism comprises counterweights mounted on linkage arms of said second spherical linkage.

18. The assembly of claim 15 further comprising a shaft and U-joint arrangement extending between said first and second spherical linkages.

19. The assembly of claim 15 wherein said parallelogram linkage and first and second spherical linkages are coupled to a linear slide assembly.

20. The assembly of claim 15 further comprising a sensor arrangement comprising a plurality of sensors at different locations on said assembly.

21. The assembly of claim 14 comprising a pair of brakes configured to selectively inhibit or permit rotation of the first spherical linkage about the first center of motion (FCOM) and the second spherical linkage about the second center of motion (RCOM).

* * * * *